United States Patent [19]

Johnson

[11] Patent Number: 5,372,608
[45] Date of Patent: Dec. 13, 1994

[54] CIRCULATING CHILLED-FLUID THERAPEUTIC DEVICE

[76] Inventor: Bertrand L. Johnson, 1018 Cosimano Pl., West River, Md. 20778

[21] Appl. No.: 105,917

[22] Filed: Aug. 12, 1993

[51] Int. Cl.⁵ .............................................. A61F 7/00
[52] U.S. Cl. ................................. 607/104; 607/111; 607/112
[58] Field of Search .................... 607/96, 108–112, 607/114, 104

[56] References Cited

U.S. PATENT DOCUMENTS

| | | |
|---|---|---|
| 222,690 | 12/1879 | Goldschmidt .................... 607/104 |
| 301,931 | 7/1884 | Smith et al. . |
| 400,261 | 3/1889 | Small ............................. 607/104 X |
| 546,436 | 9/1895 | Springsteen .................... 607/104 X |
| 2,648,325 | 8/1953 | Siple . |
| 2,911,974 | 11/1959 | Spence . |
| 3,612,059 | 10/1971 | Ersek . |
| 3,670,518 | 6/1972 | Esposito . |
| 3,871,381 | 3/1975 | Roslonski . |
| 4,367,743 | 1/1983 | Gregory . |
| 4,459,468 | 7/1984 | Bailey . |
| 4,844,072 | 7/1989 | French et al. . |
| 4,856,294 | 8/1989 | Scaringe et al. . |
| 4,981,135 | 1/1991 | Hardy . |
| 5,072,875 | 12/1991 | Zacoi . |
| 5,077,980 | 1/1992 | Weber . |
| 5,080,089 | 1/1992 | Mason et al. . |
| 5,143,064 | 9/1992 | Cochran . |
| 5,165,400 | 11/1992 | Berke . |
| 5,170,783 | 12/1992 | Smith . |
| 5,201,365 | 4/1993 | Siegel . |

Primary Examiner—Angela D. Sykes
Attorney, Agent, or Firm—Michael M. de Angeli

[57] ABSTRACT

An improved therapeutic device for applying cooling to a body joint to speed healing comprises a reservoir of chilled fluid connected to a container in heat conducting relation with the joint to be chilled by supply and return lines. Fluid is continually recirculated by convection, employing the thermosiphon principle, such that the fluid is recirculated by energy provided by the patient's body heat. Check valves may be provided in one or both of the supply and return lines, preventing reverse flow, and also so that motion of a patient's body joint within the container further motivates the recirculating flow.

13 Claims, 1 Drawing Sheet

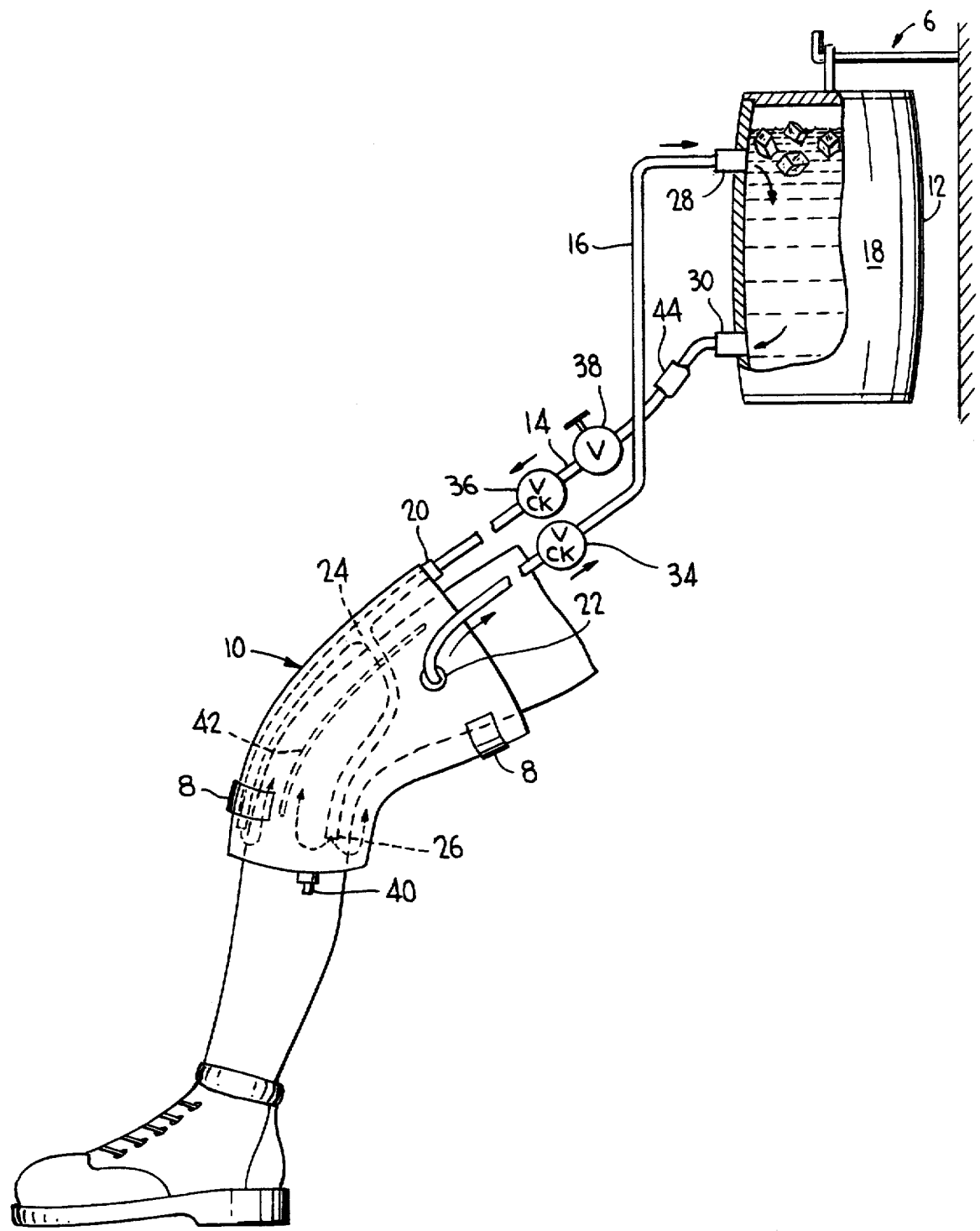

CIRCULATING CHILLED-FLUID THERAPEUTIC DEVICE

FIELD OF THE INVENTION

This invention relates to a therapeutic device for applying cooling to a body joint or the like. More particularly, the invention relates to a system for circulating chilled fluid between a reservoir of chilled fluid and a container in thermally-conductive relation to a body joint to be chilled, wherein the energy for circulating the fluid is provided by the body heat and/or movement of the patient.

BACKGROUND OF THE INVENTION

There are many patents that relate generally to the subject of application of heat and/or cooling to a patient to promote healing, reduce swelling, and the like. Many of these disclosures relate to complex apparatus; see U.S. Pat. Nos. 4,844,072 to French et al, 5,077,980 to Weber, and 5,080,089 to Mason et al. Other complex systems for regulating body temperature in adverse environments (i.e., for both heating and/or cooling) are shown in U.S. Pat. Nos. 3,670,518 to Esposito, 2,648,325 to Siple, and 5,201,365 to Siegel. Other patents generally relevant to the subject matter of the present invention include U.S. Pat. Nos. 3,612,059 to Ersek; 5,072,875 to Zacoi; 5,165,400 to Berke; 4,459,468 to Bailey; 4,367,743 to Gregory; 301,931 to Smith et al; 4,856,294 to Scaringe et al; 4,981,135 to Hardy; 5,143,064 to Cochran, and 2,911,974 to Spence.

The prior art applicable to this invention also includes U.S. Pat. Nos. 3,871,381 to Roslonski and 5,170,783 to Smith. Of these, Roslonski discloses a "cold compress device" wherein an inflatable compress is connected to a controllable source of pressurized refrigerant. As the refrigerant is controllably released into the compress, it expands, effectively cooling the compress. The fact that elevated pressures are involved limits the use of the Roslonski device.

More particularly, postoperative patients commonly benefit from chilling body joints and the like, to reduce swelling and pain, and to speed their healing. In accordance with present trends toward outpatient and self-care wherever possible, it would be desirable to provide a simple and cost-effective system for convenient cooling of body joints that would be suitable for in-home, outpatient use by a patient without assistance, as well as for hospital use.

U.S. Pat. No. 5,170,783 to Smith, referred to above, discloses a "cryotherapeutic procedure" and related apparatus that has utility for thus chilling a bone joint or the like, but has numerous shortcomings. The Smith system comprises a reservoir of chilled fluid (e.g., ice water) that is elevated with respect to a compress fitting around the joint to be chilled. A tube carries the fluid to the compress, chilling the joint; the pressure head controlled by the difference in height between the reservoir and compress controls the pressure in the compress, which may be further controlled by a flow-controlling valve in the supply line.

Accordingly, in use of the Smith device, the compress is initially filled with cold water, and is pressurized responsive to the pressure head, as above. Over time, the water in the compress will be warmed responsive to heat transfer from the limb being cooled, such that the temperature in the compress rises gradually. When it is desired to replenish the cold water in the compress, it must be drained and refilled manually. In practice, this requires frequent attention and is a substantial inconvenience.

It would be possible, of course, to provide a small pump driven by an electric motor or the like for recirculating the warm fluid from the Smith compress to the reservoir. Various of the patents referred to above show such externally-powered positively-driven personal cooling systems providing recirculation of the coolant. However, this would inevitably complicate the device, would require power cords and the like, and would increase its cost.

SUMMARY AND OBJECTS OF THE INVENTION

It is therefore an object of the invention to provide a simple and inexpensive system and method for cooling a body joint or the like for therapeutic purposes, wherein cooling fluid is recirculated between a container in thermally-conductive relation to the body joint and a reservoir of chilled fluid to maintain the container at a relatively constant temperature, without externally-powered pumps or other complexities.

The present invention satisfies the above needs of the art and object of the invention mentioned above, and others which will appear as the discussion below proceeds, by providing a system for providing therapeutic cooling to a body joint or the like comprising a reservoir of chilled fluid having a fluid supply port in a lower portion of the reservoir and a return port in the upper portion of the reservoir. A container for being secured to a body joint or the like in thermally-conductive relationship therewith is provided. The container comprises an inlet port adapted to carry chilled fluid supplied by a chilled fluid supply line connected from the supply port of the reservoir to the lower portion of the container, and an outlet port adapted to return fluid from the upper portion of the container to the return port of the reservoir by a warmed fluid return line.

In use, chilled fluid—normally a mixture of water and ice—is poured into the reservoir, and flows through the chilled fluid supply line, filling the container with cold water. The return line is also filled with water. Sufficient cold water is poured into the reservoir to cover the supply and return ports. As the water in the container is warmed due to body heat from the joint, it expands. Since the inlet port is at the lower part of the container, the expanded warmed water, having reduced density, is pushed upwardly through the return line to the reservoir according to the thermosiphon principle. Accordingly, a loop is provided for continuously recirculating the water between the reservoir and the container, thus ensuring that the container is consistently supplied with chilled water. The rate of cooling is proportional to the heat provided by the body joint, but may be further controlled by a simple flow control valve in either the supply or the return line.

In the preferred embodiment check valves are provided in one or both of the supply and return lines to ensure that flow takes place only in the proper direction, and to assist in priming of the system. Further, provision of the check valves allows any motion of the body joint—e.g., flexing the patient's leg, if the container is secured around the knee—to further drive the circulation of chilled and warmed fluids in the system. Valves and fittings to allow the lines to be shut off and disconnected provide convenient disconnection and reconnection of the container and the reservoir, to allow the patient mobility as needed without removing the container from the body joint.

BRIEF DESCRIPTION OF THE DRAWING

The invention will be better understood if reference is made to the accompanying single Figure, showing a schematic perspective view of a system according to the invention.

DESCRIPTION OF THE PREFERRED EMBODIMENT

As shown in FIG. 1, the apparatus for chilling a body joint according to the invention comprises a container 10, a reservoir of chilled fluid 12, a supply line 14 and return line 16. The container 10, which may also be referred to as a "compress" or as a "dressing" as these terms are used in the art, may, for example, comprise an envelope of flexible but nonelastic fabric material impregnated with rubber, vinyl or another plastic or the like so as to be water impermeable. Such a container may be formed by heat sealing plural impregnated-fabric layers to one another to form seams, including internal strengthening or flow-controlling baffles as needed. The container might alternatively be configured as a flexible bladder within an external fabric housing, to provide structural strength. Clearly, the configuration of the container will vary depending on the body part with which it is intended to be used. Conventionally, the container is secured around a patient's joint or another body part to be chilled (for example, a knee joint as shown) by cooperating strips 8 of Velcro TM hook and loop materials, or other known means.

The reservoir 12 (which is preferably insulated to reduce heat flux from the atmosphere) is filled with a chilled fluid, typically a mixture of ice and water, as indicated at 18. The reservoir is adapted to be supported above the container, as indicated schematically at 6. As in the case of the Smith U.S. Pat. No. 5,170,783 referred to above, the height of the reservoir above the container controls the pressure in the container. The supply line 14 is connected to a supply port 30 in fluid transfer relationship with the lower portion of the reservoir 12, such that the chilled fluid 18 flows downwardly through the supply line 14 toward the container 10. The container 10 comprises an inlet port 20 and an outlet port 22. Both the inlet port 20 and the outlet port 22 may be provided at an upper portion of the container 10 for convenient connection to the lines 14 and 16, as shown. However, if this is done, the inlet port must be connected to internal piping means 24 so that the chilled fluid 18 actually enters the internal volume of the container 10 at or near its lower extremity, as indicated generally at 26.

The chilled fluid 18 entering the container 10 at its lower extremity as shown at 26 is in heat transfer relationship with the joint of the patient to be chilled. Accordingly, the fluid in the container 10 is gradually warmed by the body heat of the patient. As the fluid is warmed, it becomes less dense and rises, that is, by convection. The warmed fluid enters the return line 16 at the outlet port 22 and rises upwardly, entering the reservoir 12 at a return port 28, below the level of the fluid 18 in the reservoir.

More specifically, a path for the chilled fluid is established from reservoir 12, through supply port 30, through the chilled fluid supply line 14, through the inlet port 20, and through the internal piping means 24, and entering the internal volume of the container 10 at its lower extremity 26. The fluid is then heated as indicated above by heat transfer from the body heat of the patient, and therefore becomes less dense, rising to enter the return line 16 at outlet port 22 and flowing into the return port 28 of the reservoir 12. A convection-driven recirculating path is thus established.

The recirculation of fluid in a closed system driven by application of heat at one point in the system, as shown, is referred to as the "thermosiphon" principle. The thermosiphon principle is well known in various systems and has been used to circulate cooling water for internal combustion engines, for example. Insofar as known to the present inventor, this principle has never been applied to a therapeutic chilling apparatus as disclosed herein.

Further improvements may include the provision of valves in the supply line 14 and the return line 16. Preferably, a check valve 36 is provided in at least one of the supply line 14 and the return line 16, to prevent reverse flow and assist in establishing proper flow through the system. If, as is preferred, the container is formed of a flexible nonelastic material, such as a fabric impregnated with rubber or vinyl or other plastic material, provision of one or both of check valve(s) 34 and 36 in the supply and/or return lines has the advantage that any motion of the patient's body joint within the container, e.g., flexing of his or her knee, will promote the recirculation of the fluid. Where not excluded by the language of the appended claims, the invention also includes this source of energy for motivating the recirculation of fluid between the reservoir and the container.

Valves 34 and 36 are preferably adapted to provide complete shut-off and quick disconnection of the lines 14 and 16, so that the patient can conveniently disconnect the lines 14 and 16 connecting the container 10 to the reservoir 12. This allows the patient to move about from time to time, without having to remove the container 10 from the joint to be chilled.

Preferably, a flow control valve 38 is also provided; as the rate of flow of fluid through the system controls the amount of cooling provided to the joint, valve 38 can be operated by the patient in accordance with his or her particular needs and desires. A drain valve 40 is also usefully provided for the convenient draining of the container as needed.

As indicated generally at 42, the container 10 may comprise internal baffles, e.g., formed by heat-sealing the top and bottom surfaces of the container together at manufacture, to control the flow of fluid through the internal volume thereof, and to preclude expansion or "ballooning" of the container due to the fluid pressure therein. Such heat-sealed seams may also be arranged to implement internal piping 24 connecting the inlet port 20 to the lower extremity 26 of container 10, so that the chilled fluid enters the container at its vertically lowest point.

As indicated schematically at 44, the supply and/or the return line may be insulated in order to limit heat gain from the atmosphere, particularly into the chilled water supply line 14.

In use, chilled fluid (typically a mixture of ice and water) is poured into the reservoir, and flows through the chilled water supply line 14 and fills the container 10. The return line 16 is also filled with water. Sufficient water must be placed in the reservoir 12 to cover the supply and return ports. As the water in the container 10 is warmed due to body heat from the joint, it expands. Since the chilled water enters the lower part of the container 10, the expanding warmed water tends to flow upwardly, exiting the container 10 through the return line 16 and entering the reservoir 12 through the return port 28, according to the thermosiphon principle. Accordingly, a loop is provided for continuously recirculating the water between the reservoir and the container, thus ensuring that the container is consistently supplied with chilled water. The rate of cooling is proportional to the heat provided by the body joint, but may be further controlled by flow control valve 38 in either the supply or the return line.

As noted above, in the preferred embodiment, check valves are provided in one or both of the supply and return lines so as to prevent reverse flow of the fluid in use. Further, if the container is manufactured of a flexible, nonelastic material, and if at least one check valve is provided, motion of a body joint about which the container is affixed will cause the container to be compressed, acting as a pump, further motivating the recirculating flow of the cooling fluid.

It will therefore be appreciated that there has been described a simple and efficient apparatus for providing recirculation of cooling water in a therapeutic system for chilling a body joint or the like. The necessity of frequently draining and refilling the container, for example, as required by the device shown in Smith U.S. Pat. No. 5,170,783, is eliminated. Moreover, as all of the energy required to circulate the fluid is provided by the body heat of the patient, or by patient motion, no pumps or other external devices are required.

It is acknowledged that some of the prior art patents referred to above recognize broadly that convection can be used to circulate liquid in a system for controlling body heat. See, for example, Siple U.S. Pat. No. 2,648,325, at column 4, lines 52–65 and U.S. Pat. No. 3,670,518 to Esposito at column 1, lines 30–33. It will be appreciated that neither Siple nor Esposito shows a system which meets applicant's claims as appended hereto and, in particular, that both Siple and Esposito show systems which are far too complicated for use by a patient without close medical supervision, if indeed such systems could even be adapted to apply cooling fluid to a body joint for postoperative therapeutic purposes as discussed herein.

While a preferred embodiment of the invention has been described, this should not be considered a limitation on the invention, which is to be measured only by the following claims.

What is claimed is:

1. A therapeutic device for chilling a body joint or the like, comprising:

a sealed, flexible, nonexpansible, collapsible container adapted to be affixed to a body joint or the like in heat transfer relationship therewith, said container defining a nonexpansible interior volume in liquid transfer relation with an inlet port and an outlet port, means for affixing said container to said body joint or the like in a predetermined position with respect to the vertical, such that said outlet port is in liquid transfer relation with substantially the uppermost portion of the interior volume of said container, and said inlet port is in liquid transfer relation with substantially the lowermost portion of the interior volume of said container, a reservoir for containing a quantity of chilled liquid, said reservoir comprising a return port in liquid transfer relation with an upper portion of said reservoir, and a supply port in liquid transfer relation with a lower portion of said reservoir;

means for securing said reservoir in a particular orientation with respect to the vertical, so as to define said upper portion and said lower portion of said reservoir, and so that said reservoir can be supported above said container in use;

a chilled liquid supply line connecting said supply port of said reservoir to said inlet port of said container;

a warmed liquid return line connecting said outlet port of said container to said return port of said reservoir; and a quantity of chilled liquid filling said container and said supply and return lines, and filling said reservoir to a point at least above said return port, whereby chilled liquid enters said container through said supply line connected to said inlet port, is warmed by body heat from the body joint to be chilled, rises through said container due to convection, and is returned to said reservoir through said return line connected to said outlet port, establishing liquid circulation motivated by body heat from the body joint to be chilled, and chilling said body joint without phase change of the circulating liquid.

2. The therapeutic device of claim 1, further comprising means for regulating the rate of flow of said liquid through at least one of said supply and return lines, whereby the effective rate of chilling of said body joint may be regulated.

3. The therapeutic device of claim 1, further comprising first and second valves in said supply and return lines, and means permitting ready disconnection of said supply and return lines, whereby said container may be readily disconnected from said reservoir.

4. The therapeutic device of claim 1, wherein one or both of said supply and return lines are insulated to limit heat gain from the atmosphere.

5. The therapeutic device of claim 1, wherein said chilled liquid is a mixture of ice and water.

6. The therapeutic device of claim 1, wherein said container is adapted to be affixed around a patient's limb, to chill a body joint in said limb.

7. The therapeutic device of claim 1, wherein said container comprises a flexible, nonelastic envelope and means for securing said envelope in a desired position around a body joint to be chilled.

8. The therapeutic device of claim 7, wherein plural internal baffles are provided within said flexible envelope.

9. The therapeutic device of claim 7, further comprising at least one check valve controlling flow through one or both of said return line and said supply line, whereby flow of said chilled liquid from said container to said reservoir and of warmed liquid from the reservoir to the container is prevented, and whereby motion of a body joint to be chilled within said envelope further augments said liquid circulation.

10. The therapeutic device of claim 1, further comprising a drain valve for draining said container.

11. A method for chilling a body joint or the like, comprising the steps of:

affixing a sealed container to a body joint or the like to be chilled in heat transfer relationship therewith, said container defining an interior volume in liquid transfer relation with an inlet port and an outlet port, said container being affixed to said body joint or the like in a predetermined position with respect to the vertical, such that said outlet port is in liquid transfer relation with substantially the uppermost portion of the interior volume of said container, and said inlet port is in liquid transfer relation with substantially the lowermost portion of the interior volume of said container;

providing a reservoir containing a quantity of chilled liquid, said reservoir having an outlet port and a return port;

securing said reservoir in a particular orientation with respect to the vertical, so as to define an upper portion and a lower portion of said reservoir, and such that said return port is in liquid transfer relation with said upper portion of said reservoir, and said supply port is in liquid transfer relation with said lower portion of said reservoir, and supporting said reservoir such that said outlet port is higher than said inlet port of said container;

providing a chilled liquid supply line connecting said supply port of said reservoir to said inlet port of said container, and a warmed liquid return line connecting said return port of said reservoir to said outlet port of said container; and filling said reservoir, said container, and said supply and return lines with chilled liquid; and permitting said chilled liquid to enter said container through said supply line connected to said inlet port, to be warmed by body heat from the body joint or the like to be chilled, to rise through said container due to convection, and to be returned to said reservoir through said return line connected to said outlet port, whereby chilled liquid circulation is established without a source of energy other than body heat from the body joint or the like to be chilled, and whereby the body joint or the like be chilled is chilled without change of phase of said liquid.

12. The method of claim 11, further comprising the step of regulating the rate of flow of said liquid through at least one of said supply and return lines, whereby the effective rate of chilling of the body joint or the like to be chilled may be regulated.

13. The method of claim 11, comprising the further step of providing at least one check valve controlling flow through one or both of said supply and return lines, whereby motion of said body joint or the like to be chilled within said container promotes said chilled liquid circulation.

* * * * *